(12) United States Patent
Ottoboni et al.

(10) Patent No.: US 8,486,444 B2
(45) Date of Patent: Jul. 16, 2013

(54) NANOBUBBLES USEFUL AS AN ULTRASONIC CONTRAST AGENT FOR THE LYMPHATIC SYSTEM

(75) Inventors: Thomas B. Ottoboni, Belmont, CA (US); Robert E. Short, Los Gatos, CA (US); Jeffrey D. Gabe, San Bruno, CA (US)

(73) Assignee: University of Pittsburgh-of the Commonwealth System of Higher Education, Pittsburg, PA (US)

( * ) Notice: Subject to any disclaimer, the term of this patent is extended or adjusted under 35 U.S.C. 154(b) by 0 days.

(21) Appl. No.: 13/209,917

(22) Filed: Aug. 15, 2011

(65) Prior Publication Data
US 2012/0034170 A1 Feb. 9, 2012

Related U.S. Application Data

(63) Continuation of application No. 11/781,209, filed on Jul. 20, 2007, now abandoned, and a continuation of application No. 09/637,516, filed on Aug. 11, 2000, now abandoned.

(60) Provisional application No. 60/148,892, filed on Aug. 13, 1999.

(51) Int. Cl.
*A61B 8/00* (2006.01)
*A61K 9/127* (2006.01)
*A61K 9/14* (2006.01)

(52) U.S. Cl.
USPC .......................... 424/450; 424/489; 424/9.51

(58) Field of Classification Search
USPC ........................ 424/450, 489, 9.51
See application file for complete search history.

(56) References Cited

U.S. PATENT DOCUMENTS

| | | | |
|---|---|---|---|
| 3,743,604 A | 7/1973 | Schnoring et al. | 427/213.35 |
| 4,718,433 A | 1/1988 | Feinstein | 424/9.52 |
| 4,880,634 A | 11/1989 | Speiser | 424/450 |
| 5,041,292 A | 8/1991 | Feijen | 424/484 |
| 5,271,961 A | 12/1993 | Mathiowitz et al. | 427/213.31 |
| 5,310,540 A | 5/1994 | Giddey et al. | 424/9.52 |
| 5,333,613 A | 8/1994 | Tickner et al. | 600/458 |
| 5,425,366 A | 6/1995 | Reinhardt et al. | 600/458 |
| 5,496,536 A | 3/1996 | Wolf | 424/9.322 |
| 5,501,863 A | 3/1996 | Rossling et al. | 424/489 |
| 5,518,709 A | 5/1996 | Sutton et al. | 424/9.52 |
| 5,542,935 A | 8/1996 | Unger et al. | 604/190 |

(Continued)

FOREIGN PATENT DOCUMENTS

| | | |
|---|---|---|
| DE | 4416 818 | 11/1995 |
| EP | 0 224 934 | 2/1989 |

(Continued)

OTHER PUBLICATIONS

De Cicco, et al., "Intraoperative localization of the sentinel node in breast cancer: technical aspects of lymphoscintigraphic methods." *Semin Surg. Oncology* 15:268 (1998).

(Continued)

*Primary Examiner* — San-Ming Hui
(74) *Attorney, Agent, or Firm* — Medlen & Carroll, LLP (57) ABSTRACT

A composition is provided accompanying nanoparticles having diameters in the range of about 100 to 800 nanometers with hollow cores and outer shells with mechanical properties such that they rupture on exposure to predetermined ultrasound energy. The composition is useful for identifying sentinel lymph nodes.

26 Claims, 4 Drawing Sheets

U.S. PATENT DOCUMENTS

| | | | | |
|---|---|---|---|---|
| 5,560,364 | A | 10/1996 | Porter | 600/458 |
| 5,562,893 | A | 10/1996 | Lohrmann | 424/9.52 |
| 5,565,215 | A | 10/1996 | Gref et al. | 424/501 |
| 5,569,468 | A | 10/1996 | Modi | 424/491 |
| 5,611,344 | A | 3/1997 | Bernstein et al. | 600/438 |
| 5,620,883 | A | 4/1997 | Shao et al. | 435/174 |
| 5,679,377 | A | 10/1997 | Bernstein et al. | 424/491 |
| 5,707,607 | A | 1/1998 | Quay | 424/9.52 |
| 5,711,933 | A | 1/1998 | Bichon et al. | 424/9.52 |
| 5,730,955 | A | 3/1998 | Lohrmann | 424/9.52 |
| 5,770,222 | A | 6/1998 | Unger et al. | 424/450 |
| 5,837,221 | A | 11/1998 | Bernstein et al. | 424/9.52 |
| 5,840,275 | A | 11/1998 | Bichon et al. | 424/9.52 |
| 5,863,520 | A | 1/1999 | Bichon et al. | 424/9.52 |
| 5,919,434 | A | 7/1999 | Dugstad et al. | 424/9.52 |
| 5,922,304 | A | 7/1999 | Unger | 424/9.3 |
| 5,948,387 | A | 9/1999 | Unger et al. | 424/9.5 |
| 6,028,066 | A | 2/2000 | Unger | 514/180 |
| 6,068,857 | A | 5/2000 | Weitschies et al. | 424/489 |
| 6,120,805 | A | 9/2000 | Spenlehauer et al. | 424/489 |
| 6,171,246 | B1 | 1/2001 | Averkiou et al. | 600/438 |
| 6,193,951 | B1 | 2/2001 | Ottoboni et al. | 424/9.5 |
| 6,200,548 | B1 | 3/2001 | Bichon et al. | 424/9.51 |
| 6,205,352 | B1 | 3/2001 | Carroll | 600/431 |
| 6,207,135 | B1 | 3/2001 | Rossling et al. | 424/9.52 |
| 6,224,554 | B1 | 5/2001 | Tickner et al. | 600/438 |
| 6,444,192 | B1 | 9/2002 | Mattrey | 424/9.52 |
| 6,521,211 | B1 | 2/2003 | Unger et al. | 424/9.52 |
| 2002/0159952 | A1 | 10/2002 | Unger | 424/9.51 |
| 2003/0003055 | A1 | 1/2003 | Unger et al. | 424/9.51 |

FOREIGN PATENT DOCUMENTS

| | | |
|---|---|---|
| EP | 0 398 935 | 11/1990 |
| EP | 0 441 468 | 8/1991 |
| EP | 0 523 183 | 10/1991 |
| EP | 0 458 745 | 11/1991 |
| EP | 0 512 693 | 11/1992 |
| EP | 0 681 843 | 11/1995 |
| GB | 2256183 | 12/1992 |
| WO | WO 91/12823 | 9/1991 |
| WO | WO 92/18164 | 10/1992 |
| WO | WO 98/48783 | 11/1998 |
| WO | WO 98/48838 | 11/1998 |
| WO | WO 0012062 | 3/2000 |
| WO | WO 0112069 | 2/2001 |

OTHER PUBLICATIONS

De Cicco, et al., "Lymphoscintigraphy and radioguided biopsy of the sentinel axillary node in breast cancer." *Nuclear Med.* 39:2080 (1998).

Linehan, et al., "Sentinel lymph node biopsy in breast cancer: unfiltered radioisotope is superior to filtered." *Am. Coll. Surgery* 188:377 (1999).

Medwin, et al., "Counting Bubbles Acoustically: a Review", Ultrasonics, pp. 7-14 (1977).

Paganelli, et al., "Optimized sentinel node scintigraphy in breast cancer." *Q J Nuclear Medicine* 42:49 (1998).

Kremkau, et al., "Diagnostic Ultrasound: Principles, Instruments & Exercises." 5$^{th}$ Edition, W.B. Saunders Company (1998).

Lubbers J, Van den Berg JW. "An ultrasonic detector for microgas emboli in a bloodflow line." *Ultrasound Med Biol.* 2:301-310 (1977).

Andre, et al., "Physical and Acoustical Properties of Perfluorooctylbromide an Ultrasound Contrast Agent," *Invest Radiol.* 25(9):983-7 (1990).

Andre, et al., "Enhancement of the echogenicity of flowing blood by the contrast agent perflubron." *Invest Radiol.* 28(6):502-6 (1993).

Forsberg, et al., "Physics of Contrast Microbubbles." In *Ultrasound Contrast Agents: Basic Principles and Clinical Applications*. Goldberf, BB, Raichlen JS, and Forsberg, F. Martin Dunitz (eds.) pp. 15-24 (2001).

Hughes, et al., "Comparison of ultrasound scattering properties of Optison(R) with a liquid perfluorocarbon nanoparticle contrast agent." Ultrasonics Symposium, 2001 IEEE, pp. 1675-1678 (2001).

Mattrey, et al., "Perfluoroctylbromide: a liver/spleen-specific and tumor-imaging ultrasound contrast material." *Radiology* 145:3:759-762 (1982).

Ngo, et al., "Evaluation of liquid perfluorocarbon nanoparticles as a blood pool contrast agent utilizing power Doppler harmonic imaging." Ultrasonics Symposium, 2000 IEEE, 1931-1934 vol. 2 (2000).

Ottoboni, et al., "Microparticles Useful as Ultrasonic Contrast Agents and for Drug Delivery." Database Derwent on East AN 1999-009363 (1999).

PCT Search Report PCT/US00/22097, Oct. 13, 2000.

Swartz, "The physiology of the lymphatic system." *Adv Drug Deliv Rev.* 50(1-2):3-20 (2001); and.

Bazile, et al., "Body Distribution Of Fully Biodegradable [14C]-Poly(Lactic Acid) Nanoparticles Coated With Albumin After Parenteral Administration To Rats." *Biomaterials* 13(15):1093-1102 (1992).

NANOBUBBLES USEFUL AS AN ULTRASONIC CONTRAST AGENT FOR THE LYMPHATIC SYSTEM

CROSS REFERENCE TO RELATED APPLICATIONS

This application is a continuation application of application Ser. No. 09/637,516 filed Aug. 11, 2000, which claims benefit under 35 U.S.C. §119(e) to application Serial No. 60/148,892, filed Aug. 13, 1999, the disclosures of which are incorporated herein by reference in their entirety.

FIELD OF THE INVENTION

This invention relates to hollow gas-filled Nanoparticles in a size range optimized for uptake by the lymphatic system and to their method of use in identifying sentinel lymph notes around tumors by means of echographic imaging techniques.

BACKGROUND OF THE INVENTION

Solid tumor cancers often spread through lymph channels to regional lymph nodes. Because of this tendency, elective lymph node dissection has become a recognized treatment for patients with early stage melanoma, breast, and other cancers. Many surgeons believe that elective lymph node dissection in a patient with micrometastases can prolong the patient's life and, if conducted early enough, cure the disease. Elective lymph node dissection, however, benefits only those patients with micrometastases and is unnecessary in many cases. This is a matter of concern because dissection of the entire lymphatic drainage basin is a major surgical procedure associated with a number of potential short- and long-complications including increased surgical trauma and scarring, risk of nerve damage, possible reduced immune system function, and lymphedema.

Sentinel lymph node identification and dissection is a relatively new technique wherein the surgeon performs a biopsy of a few of the lymph nodes surrounding the tumor of a cancer patient to determine if the tumor has metastasized to those lymph nodes near the tumor. These so-called "sentinel nodes" are the first nodes that receive drainage from lymph ducts around a tumor. Studies have shown that the pathologic status of the sentinel nodes accurately predicts the status of all the lymph nodes along the drainage path. Thus, if the sentinel nodes are free of metastatic cells, the other subsequent nodes are most likely free of cancer as well and formal lymphadenectomy (and its associated morbidity) can be avoided.

Current techniques for the identification of sentinel lymph nodes involve the subcutaneous injection of visible dyes and/or colloidal radioactive tracers around a tumor. After allowing time for the peripheral uptake of these materials into the lymphatic system and their migration to the sentinel nodes, the nodes are localized visually or with a gamma probe, respectively. The use of radioactive tracers and gamma probes has the added benefit of being non-invasive. Sentinel nodes identified by either method can then be removed entirely or samples of tissue removed for evaluation by a pathologist. In some cases the tissue sample is collected by aspiration with a fine needle using ultrasound to guide the collection.

Other imaging technologies such as computerized tomography (CT) and magnetic so resonance imaging (MRI) have historically been used to aid in the examination of lymph nodes and the identification of cancerous nodes that are grossly altered in their size or structure. Lymphatic contrast agents for CT and MRI, such as iodinated nanoparticles, perfluorobromide emulsions, gadolinium diethylenetriaminepentaacetic acid and colloidal magnetite have been used to enhance images with these modalities. These technologies can only detect the presence of a sizeable, well-defined tumor mass and have not been routinely applied to the identification of the sentinel nodes.

Sonography has also been used for imaging cancerous lymph nodes. Intravenous injection of microbubbles derived from the dissolution of galactose has been used as an ultrasound contrast agent to assess the vascular architecture of suspected cancerous lymph nodes. However, application of this imaging modality for sentinel node identification has not heretofore been considered because an ultrasonic contrast agent with the necessary size spectrum and acoustic properties has yet to be described.

It is well known that gas-containing microparticles, sometimes called microbubbles, are efficient backscatterers of ultrasound energy. Thus, microbubbles injected interstitially or into the bloodstream can enhance ultrasonic echographic imaging to aid in the visualization of biological structures such as the internal organs or the cardiovascular system. Contrast is achieved when acoustic impedance between two materials at an interface is different. Thus, the greater the impedance difference between the two materials the greater the intensity of the ultrasound echo. Since there is a large difference between the acoustic impedance between body tissue and gas, microbubbles offer excellent ultrasound contrast to aid in delineating biological structures that otherwise would be difficult to distinguish.

There are a number of commercially available ultrasound systems commonly used for imaging biological tissues. Each of these instruments offer the user the ability to select from a variety of transducers with different acoustic characteristics and provide different imaging modes to detect and process the sound waves. Choice of transducer and imaging mode to be employed depends upon factors influencing the acoustic characteristics of the specific regions to be imaged. These factors include the distance from the transducer, the density or type of the target tissue and adjacent or intervening tissues, use of contrast agent, and blood flow. A detailed description of the principles of ultrasound including the variety of transducer types, the different imaging modes (B-mode, power doppler, pulse inversion, etc.) and the factors influencing their use can be found in Diagnostic Ultrasound by Frederick W. Kremkau.

Most current applications for echographic contrast rely upon the intravascular injection of the agent and its delivery to the area of interest via the bloodstream. These contrast agents must be small enough to traverse the vascular system but should be as large as possible to maximize backscatter for ease and sensitivity of detection. For example, contrast agents used for visualizing cardiac function are typically injected intravenously.

Before agent can perfuse the tissues of the heart, it must first pass through the pulmonary capillary network. As a result of these competing demands, the practical size range of vascular contrast agents is approximately 1 to 10 microns in diameter. Larger bubbles, though more easily detected, fail to pass through the capillary network and smaller bubbles, though unrestrained by the capillary network, are detected pooly.

Microbubbles in the 1 to 10 micron size range, however, are not suitable for use in the lymphatic system. Passive entry is constrained by the dimensions of openings of the initial lymphatic vessels. Numerous studies in animals using the interstitial delivery of particles of different sizes have demonstrated that, as particle size increases, accumulation in the lymphatic system decreases. While particulate entry into the lymphatic system is also influenced by other factors such as particle surface characteristics and the physical motion or massage of the tissue at the site of delivery, absolute maximum particle size limits seem to be around one micron in diameter or, more specifically, in the 0.5 to 1 micron range. The increasing clinical use of radioactive tracers for sentinel node identification in humans afflicted with either melanoma or breast cancer provides additional data regarding particulate uptake by the initial lymphatics which is generally consistent with the data generated from animal studies. There are currently three commonly used technetium-99m labeled colloidal tracers used for lymphoscintigraphy. These are albumin, sulfur, and antimony trisulfide. Each are characterized by different physicochemical properties, including size. There is as yet no consensus on the optimal radiopharmaceutical agent for sentinel node identification.

It may be that different agents are more or less effective depending upon the location of the tumor or other factors. Nevertheless, a number of studies report improved detection with colloids of larger size (200-1000 nm) relative to smaller colloids (<200 nm) (See for example: Paganelli et al, Q J Nuclear Medicine 42, 49 (1998); De Cicco et al, Semin Surg. Oncology so 15, 268 (1998); De Cicco et al, 3. Nuclear Med. 39, 2080 (1998); Linehan et al, 3. Am. Coll. Surgery 188, 377 (1999)).

In U.S. Pat. No. 5,496,536, a method of diagnosing disease of the lymph nodes by means of lymphography is disclosed comprising the use of a contrast agent in colloidal or particulate form wherein the mean particle size is between 5 and about 900 nanometers.

Solid and liquid particles, and particularly those less than a micron in diameter, have been shown to be poor backscatterers of ultrasound and hence have not traditionally been useful as echographic contrast agents. Air trapping particles of a size range of less than about 900 nanometers, while potentially superior to solid or liquid nanoparticles, presents special challenges not only in their manufacture but also for optimizing a lymphatic ultrasound contrast agent due to the influence of size on its acoustic properties. Such a gas-filled nanoparticle shalt hereafter be referred to as a nanobubble.

Incident signals from the ultrasonic scanner interact with the bubbles and a portion of this energy is reemitted back to the sender, which generated the signals initially. The amount of backscatter, $II_s$, depends upon the bubble's scattering cross-section and the intensity of the emitted signal. Medwin (Medwin, H., "Counting Bubbles Acoustically: a Review", Ultrasonics 15 Jan 1977, pp 7-14.)discussed this process and gives, $$II_s = I_e * \sigma_{bs} \qquad (1)$$

where $I_e$ is the local intensity of the emitted ultrasonic signal, and $\sigma_{bs}$ is the bubble scattering cross-section.

The scattering cross-section is a physical property of the bubble. Equation 1 holds for intact or ruptured bubbles. However, the scattering cross-section in ruptured bubbles changes from that of intact bubbles. In some cases, it increases, thus making bubbles more echogenic. Sometimes it decreases making bubbles less echogenic. Agents with the higher scattering cross-section produce more backscatter which in turn is manifested electronically by the scanner as a brighter 2D signal on the monitor of the ultrasound scanner. Bright or intense areas on the monitor are more easily identified by the physician and therefore preferable.

Commercial microbubble agents and those in development typically run between 1 and 10 microns in diameter and such agents are clearly visible using ultrasonic scanners.

However, due to a of this rapid drop-off of signal with diameter, signal levels can quickly fall below the measurement threshold. Thus backscatter from intact nanobubbles normally cannot be detected. Resonant encapsulated nanobubbles with diameters around 0.5 microns are echogenic but, because of the Rayleigh effect, fall into the class of undetectable bubbles.

There is a significant increase in backscatter of nanobubbles when the ultrasonic power exceeds an MI (the inflection point on the Al) v. intensity curve at which the bubbles begin to rupture). All measurements made below this critical MI, that the backscatter is not measurable.

A feature of the invention is that it enables the identification of sentinel lymph nodes using ultrasound to detect the localized accumulation of a subcutaneously injected acoustic tracer. In addition to providing a non-invasive and less expensive sentinel node identification system, the acoustic lymphatic contrast agent of the invention integrates the techniques used for both the localization and subsequent collection of samples for analysis. Moreover, resolution of ultrasonic images of lymph node structure and provides additional information is capable of being provided relating to the condition of individual lymph nodes. The present invention also provides an acoustic lymphatic contrast agent which, when administered intravenously, accumulates in lymph nodes throughout the body allowing for enhanced ultrasonic imaging and diagnosis.

SUMMARY OF INVENTION

The present invention provides compositions of gas filled nanoparticles of which a majority has a diameter within the range of about 100 to 800 nanometers. The nanobubbles comprise an outer shell and a hollow core with the shell preferably comprising an outer layer of a biologically compatible material and an inner layer comprising a biodegradable polymer. Preferably, the outer layer is chosen on the basis of its interaction with biological tissues, cells, or fluids, whereas the inner layer is selected on the basis of desired mechanical and acoustic properties.

The nanobubble shell possesses mechanical properties so that they rupture when exposed to an ultrasound signal at powers and frequencies suitable for echographic imaging. Methods for echographically imaging the lymph system to identify the sentinel nodes around a cancer tumor using nanobubbles with mechanical properties have been selected to cause rupture upon exposure to ultrasound are also provided.

DESCRIPTION OF THE PREFERRED EMBODIMENT

As used herein the term nanobubble is intended to include capsules, spheres, and particles which are less than one micron in diameter, are hollow, and contain a gas. It is not necessary for the nanobubbles to be precisely spherical although they generally will be spherical and described as having average diameters. If the nanobubbles are not spherical, then they are referred to as having a diameter corresponding to a spherical nanobubble enclosing approximately the same volume of interior space.

The nanobubbles according to the present invention preferably have a bi-layered shell. The outer layer of the shell is a biologically compatible material since it defines the surface which will be exposed to the blood, tissues, and lymph. The inner layer of the shell is a biodegradable polymer, which may be a synthetic polymer, and may be tailored to provide the desired mechanical and acoustic properties to the shell. The outer layer of the nanobubble is distinct and continuous and is attached to the inner polymer layer by non-covalent adhesion.

The cores of the nanobubbles contain gas, typically air or nitrogen, but may also contain less water soluble gases such as a perfluorocarbon. The nanobubbles are constructed herein such that the majority of those prepared in the composition will have diameters within the range of about one hundred to eight hundred nanometers. It is in this size range that the nanobubbles are optimized for entry into and retention by the lymph system.

Figure 1:
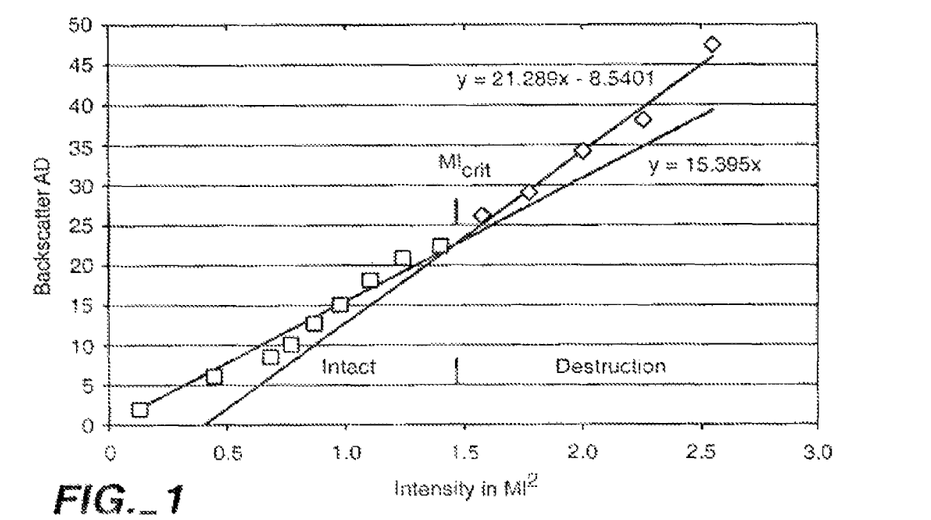
FIG. 1 is a plot of the acoustic densitometric measurement vs. intensity for a micronbubble.

An example of one such microbubble that is more robust that others is presented in FIG. 1. The backscatter AD is plotted as a function of intensity. Note that there is an inflection point in the data at the point where bubbles begin to be destroyed by the sound beam. Since the slope of the curve on the right hand side of the inflection point, referred to as the critical MI ($MI_{crit}$), is greater than on the left hand side of $MI_{crit}$, it indicates that the scattering cross-section is greater for the agent being destroyed.

Figure 2:
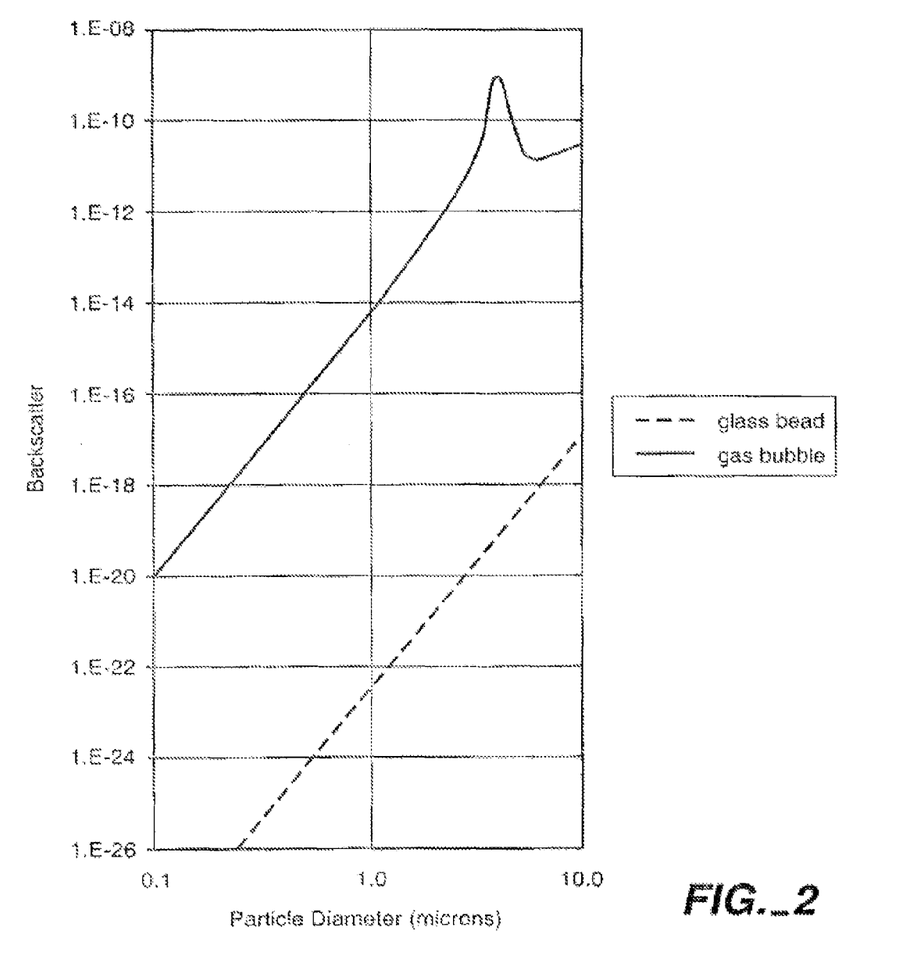
FIG. 2 is a plot of the measured backscatter vs. particle diameter of solid glass beads and gas bubbles.

Backscatter as a function of diameter is presented in FIG. 2 based upon the work of Lubbers and Van den Berg[2]. Intact bubbles exhibit a well known enhanced acoustic response known as the resonant response if the excitation frequency is somewhat close to the resonant frequency of the bubble. In this figure, a resonant response is responsible for the peak at 4 microns. Because of the increased response resulting from resonant backscatter manufacturers try to produce 4-micron bubbles. It can be seen in FIG. 2 that for bubble diameters less than 4 microns there is a significant drop-off in scattering cross-section with decreasing diameter. Note that the curve is a log-log plot so the drop-off is even more dramatic. The downward slope of backscatter intensity falls off by the power of the diameter. This phenomena is known as the Raleigh Effect. The backscatter from a 500 nanometer diameter nanobubble is about 100,000,000 times less than the peak value of a resonant, 4-micron bubble.

Solid particles are also shown in FIG. 2 for reference. It can be seen in FIG. 2 that solid particles, like bubbles, exhibit Rayleigh Scattering. Also note that bubbles are 100,000,000 fold superior backscatterers than solid particles at the same diameter.

Figure 3:
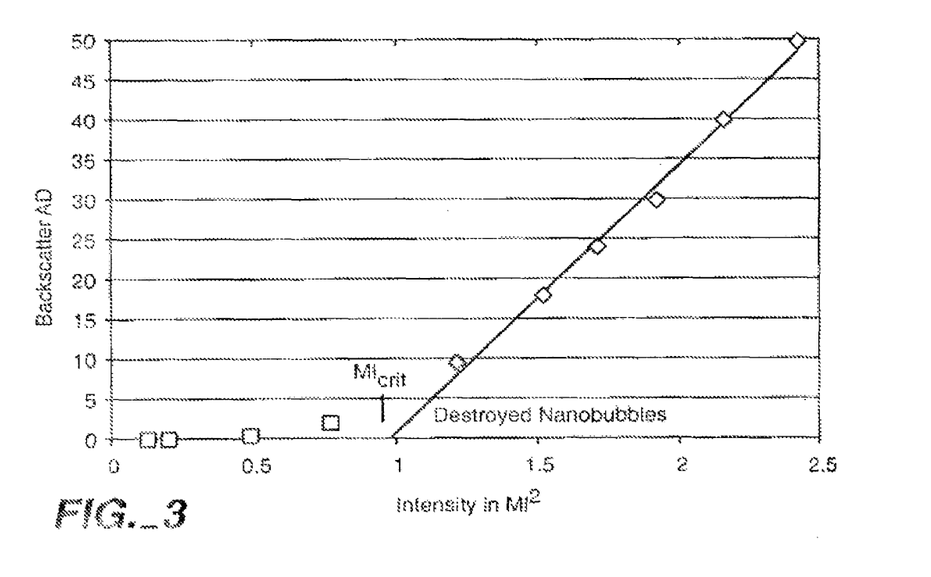
FIG. 3 is a plot of backscatter vs. intensity of a d-micron capsule with a thick wall.

As pointed out above, scattering cross-section changes dramatically when bubbles are ruptured. An example of this effect on a nanobubble is presented in FIG. 3 which shows the backscatter as measured by the HP 5500 Sonos operated in the harmonic mode. For this particular nanobubble, it can only be detected ultrasonically when being ruptured.

Since in the preferred embodiment the nanobubbles each have a distinct outer and inner layer, the layers can be tailored separately to serve different functions. The outer layer, which is exposed to the body tissues, serves as the biological interface between the nanobubbles and the body. Thus it will be made of a biocompatible material. Preferred is a material that is also amphiphilic, that is, has both hydrophobic and hydrophilic characteristics. Such preferred materials are biological materials including proteins such as collagen, gelatin or serum albumin or globulins, either derived from humans or having a structure similar to the human protein, glycosoaminoglycans such as hyaluronic acid, heparin and chondroiten sulphate and combinations or derivatives thereof. Synthetic polymers such as polyvinyl alcohol may also be used. This separate outer layer also allows for the versatility of materials suitable for charge and chemical modification. Altering the charge of the outer layer may be accomplished, for example, by using a type A gelatin with an isoelectric point above physiologic pH as opposed to a type B gelatin having an isoelectric pH below physiologic pH. The outer surface may also be chemically modified to enhance biocompatibility such as by pegylation, succinylation or amidation. Perhaps more importantly for use in lymphatic imaging, the outer surface may be comprised of, modified by, or conjugated with substances, such as Immunoglobulin 0, to specifically enhance the lymphatic uptake and/or retention of the nanobubbles. It is known that macrophage cells reside within and are capable of entering the lymphatic system. Adsorption and phagocytosis of the nanoparticles by macrophages is facilitated by the presence of IgG on the surface of these nanoparticles via the Fc receptors on the macrophage surface. Delivery of an IgG coated lymphatic acoustic contrast agent to target tissues could be enhanced via transport by macrophages. This route of delivery could provide a means for introducing larger particles which would not normally enter the lymphatic system, increased local concentration of contrast agent and prolonged retention in lymphatic tissues. Other surface modifications may include chemically binding to the surface targeting moiety for binding to selected tissues. The targeting moieties may be antibodies, cell receptors, lectins, selectins, integrins or chemical structures or analogues of the receptor targets of such materials.

Typically, the outer layer is rendered water insoluble by a cross-linking agent, such as an aldehyde or a carbodiimide. Cross-linking of the outer layer, in addition to insuring that its components are not desorbed during processing, also provides for a contiguous scaffolding upon which the inner layer is precipitated. Thus the construct of the bi-layered shell is one wherein the inner and outer layers are not covalently linked.

The inner layer will be a biodegradable polymer which may be a synthetic polymer. An advantage of a separate inner layer is that it can provide mechanical and acoustic properties to the nanobubble shell which are not provided or insufficiently provided by the surface layer without the limitations imposed by requirements of surface biointeraction. For to example, a biocompatible outer layer of a cross-linked proteinaceous hydrogel can be physically supported using a high modulus synthetic polymer as the inner layer. The polymer may be selected for its modulus of elasticity and elongation, which define the desired mechanical properties. Typical biodegradable polymers include polycaprolactone, polylactide, polyglycolide, polyhydroxybutrate, polyhydroxyvalerate, and their co-polymers; delta-valerolactone; polyalkylcyanoacrylates, polyamides, polydioxanones, poly-beta-aminoketones, polyanhydrides, poly-(ortho) esters, polyamino acids such as polyglutamic and polyaspartic acids.

The inner layer will typically have a thickness which is no larger than is necessary to meet the minimum mechanical properties in order to maximize the interior gas volume of the nanobubble. The greater the gas volume within the nanobubble the better the echogenic properties. The combined thickness of the outer and inner layers of the nanobubble shell will depend in part on the mechanical properties required of the nanobubble but typically the total shell thickness will be in the range of 20 to 100 nanometers.

In the preferred embodiment, the nanobubbles are prepared by an emulsification process wherein the respective layers are formed by sequential interfacial deposition of the selected shell materials. Due to the amphiplillicity of the material forming the outer layer, stable oil-water emulsions may be prepared having an inner phase to outer phase ratio approaching 3:1 without phase inversion. This concentrated emulsion can then in turn be diluted in water to form a stable suspension of organic phase droplets without the need for surfactants, viscosity enhancers, or high shear rates.

As a first step in the preparation, two solutions are prepared. One is an aqueous solution formed from the amphiphilic biocompatible material. This becomes the outer continuous phase of the emulsion system. The second is made from the dissolution of the biodegradable polymer in a mixture of two water immiscible organic liquids. One of the organic liquids is a relatively volatile solvent for the polymer and the other is a relatively non-volatile non-solvent for the polymer. The relatively non-volatile non-solvent is typically a C6-C20 hydrocarbon such as decane, undecane, cyclohexane, cyclooctane and the like. The relatively volatile solvent is typically a C5-C7 ester such as isopropyl acetate. Other polymer solvents, methylene chloride for example, may be used so long as they are miscible with the accompanying non-solvent.

The polymer solution (inner organic phase) is added to the biocompatible material solution (outer aqueous phase) with agitation to form an emulsion. Typically, about one part of the organic solution having a concentration of about 0.5 to 10 percent of the polymer is added to two parts of the aqueous solution having a concentration of about 1 to 20 percent of the biocompatible material. The relative concentrations of the solutions and the ratio of organic phase to aqueous phase utilized in this step will determine the thickness of the nanobubble shell.

A variety of devices can be used to produce the emulsion, e.g. colloid mills, rotor/stator homogenizers, high pressure homogenizers, and ultrasonic homogenizers. It is the emulsification step that essentially determines the diameter of the nanobubble. Thus, in order to produce nanobubbles in the 100 to 800 nanometer size range, the emulsification device must provide sufficient shear to produce organic droplets within this size range.

The emulsion is then diluted into a water bath with moderate stirring. While not intending to be bound by a particular theory, it is believed that because of its amphiphilic properties, the biocompatible material is adsorbed onto the surface of the polymer containing organic droplet during emulsification. In addition to stabilizing the emulsion, this process thus forms an envelope of the biocompatible material around the droplet. Addition of a cross-linking agent renders the biomaterial envelope insoluble thereby preventing the biocompatible material from desorbing from the surface of the organic droplet. It is this cross-linked envelope that becomes the outer layer of the nanobubble shell.

Stirring is continued while maintaining a bath temperature appropriate for the relatively volatile solvent to evaporate while the relatively non-volatile non-solvent remains As the solvent volatilizes, polymer concentration in the droplet increases to a point where it precipitates in the presence of the less volatile non-solvent. This process forms a film of polymer at the interface with the inner surface of the biomaterial layer, thus forming the inner layer of the nanobubble shell. The core of the nanoparticle then contains predominantly the organic non-solvent. The nanoparticles may then be retrieved and washed by centrifugation and diafiltration.

It may be desirable to further modify the surface of the nanobubble, for example, to enhance peripheral uptake, transport, and localization of nanobubble agent by lymph nodes. This may be accomplished, for example, by chemically conjugating immunoglobulins such as IgG to the outer biocompatible material layer. This chemistry may be performed either prior to or subsequent to drying the nanoparticles although prior to drying is preferred. Also, the hydrophilicity of the surface may be changed by attaching hydrophilic conjugates, such as polyethylene glycol (pegylation) or succinic acid (succinylation) to the surface.

The biocompatible material surface may also be modified to provide targeting characteristics for the nanobubble. The surface may be tagged by known methods with antibodies or ligands for biological receptors. For example, if the nanobubbles were treated to target lymphatic tumors, they could be used to enhance their detection by ultrasound.

The preparation process is completed by formulating the nano-sized capsules in a buffered suspending medium, and drying. The preferred drying method is by lyophilization which removes both the water and the non-solvent liquid core of the nanoparticle to yield discrete nanobubbles suspended in dry cake.

For best results the suspending medium will contain ingredients to inhibit nanocapsule aggregation prior to lyophilization and to facilitate dispersion of the nanobubbles upon reconstitution. Ingredients useful for this purpose include surfactants such as the polyoxyalkylene fatty add esters (Tween®) and the poloxamers (Pluronic®). Bulking agents and cryoprotectants are also preferably included in the suspending medium. Such materials include sugars such as mannitol, sucrose, lactose, and sorbitol; synthetic water soluble polymers such as polyethylene glycol, polyvinyl pyrrolidone, and dextran; and amino acids such as glycine, arginine, and aspartic acid. Physiologically acceptable buffering salts, sodium phosphate for example, may also be a useful ingredient in the suspending medium. Care must be taken however since the ionic nature of such salts can modify the charge and character of the surface of the nanobubble sufficiently to create adverse effects such as aggregation.

The bulking agents utilized during lyophilization of the nanoparticle suspension may also be used to control the osmolality of the final formulation for injection. An osmolality other than physiologic may be desirable during lyophilization to minimize aggregation. However, when reconstituting the nanobubbles for use, the volume of liquid used for reconstitution must take this into account.

It will be realized that various modifications of the above-described processes may be made without departing from the spirit and scope of the invention. For example, the shell of the nanobubble need not be of a bi-layered construct. By using say, a surfactant in lieu of a cross-linkable amphiphilic biomaterial in the aqueous outer phase, a mono-layer wall construct would be provided. Or, in the case of a bi-layered wall, the wall thickness of both inner and outer layers may be adjusted by varying the concentration of the components in the microparticle-forming solutions. The mechanical properties of the nanobubbles may be controlled, not only by the total shell thickness, but also by selection of materials used in each of the layers by their modulus of elasticity and elongation, and degree of crosslinking of the outer layer. Mechanical properties of the layers may also be modified with plasticizers or other additives. Precise acoustical characteristics of the nanobubble may be achieved by control of the shell mechanical properties, thickness, as well as by selective filtration to produce a narrowed size distribution, The following examples are provided by way of illustration but are not intended to limit the invention in any way.

EXAMPLE 1

Preparation of Albumin Coated Polycaprolactone Nanobubbles

A 6% aqueous solution was prepared from a 25% solution of USP grade human serum albumin (HSA) by dilution with deionized water. Separately, 1 part by weight polycaprolactone and 5 parts cyclooctane were dissolved in 55 parts isopropyl acetate at approximately 70° C. Once dissolution was complete, the organic solution was then thoroughly emulsified into an equal volume of the prepared HSA solution using a rotor/stator homogenizer. The emulsion was then diluted into 17 volumes of deionized water maintained at 30° C. and containing glutaraldehyde to crosslink the HSA. During the addition, the pH of the bath was monitored to insure that it remained between 7 and 8. Low shear mixing was continued for approximately 2 ½ hours until the isopropyl acetate had completely volatilized. Poloxamer 188 was then dissolved into the bath. Final concentration of the poloxamer was 0.25%. The suspension was allowed to come to room temperature and then centrifuged at 400 rpm for 20 minutes. The larger nanocapsules which had creamed as a result of the centrifugation were retrieved and discarded. The subnatent which contained the smaller microcapsules was then diafiltered using a 0.65 μm ultrafiltration cartridge and then concentrated to approximately one tenth the original volume. The concentrated microcapsule suspension was formulated into lyophilization excipient and then freeze dried.

The dried product was reconstituted using deionized water and viewed under the microscope. Microscopic inspection revealed very small discrete nanocapsules.

Nanobubble diameter was determined using a Malvern Micro Particle Size Analyzer. The volumetric peak diameter was determined to be 0.7 μm. The nanobubble population showed no diameter greater than 3 μm.

EXAMPLE 2

Preparation of Albumin Coated Polylactide Nanobubbles

A 50.0 gm 6% aqueous solution was prepared from a 25% solution of USP grade human serum albumin by dilution with deionized water. Separately, a 25 gm organic solution containing 0.98% poly-d,1-lactide, 6.91% cyclooctane, and 92.1% isopropyl acetate. The organic solution was then thoroughly emulsified into the prepared aqueous solution using a Virsonic sonicator homogenizer. The emulsion was then diluted into 350 ml deionized water maintained at 30° C. and containing 1.25 ml of 1N NaOH. After the emulsion was fully dispersed, 1.0 ml 25% gluteraldehyde was added to crosslink the HSA. During the addition, the pH of the bath was monitored to insure that it remained between 7 and 8. Low shear mixing was continued for approximately 2 ½ hours until the isopropyl acetate had completely volatilized. Poloxamer 188 in the amount of 0.75 gm was then dissolved into the bath. The suspension was allowed to come to room temperature and then centrifuged at 4500 rpm for 20 minutes. The microcapsules which had creamed as a result of the centrifugation were retrieved and discarded. The subnatant which contained the smaller microcapsules was then washed by diafiltration using a 0.2 μm ultrafiltration cartridge and then concentrated to approximately one twentieth original volume. The concentrated microcapsule suspension was formulated into a lyophilization excipient and then freeze dried.

The dried product was reconstituted using deionized water and viewed under the microscope. The microscopic inspection revealed very small discrete nanobubbles.

Nanobubble diameter was measured using a Malvern Micro Particle Size Analyzer. The volumetric peak diameter was determined to be 0.5 μm. The nanobubble distribution showed no diameter greater than 1 μm.

EXAMPLE 3

In-Vitro Acoustic Study

Nanobubbles fashioned in accordance with the procedures of Example 2 were tested for acoustic backscatter. For the study, an open loop flow circuit was assembled to include an ATS Laboratories Doppler flow phantom having a 6.0 mm diameter flow channel, a VWR variable flow mini-pump, and a 500 ml beaker positioned on a magnetic stir plate to serve as the reservoir for the nanobubble suspension. Flow through the phantom was adjusted to a rate of approximately 95 ml/min The backscatter measurements were made using an an HDI 5000 ultrasound system equipped with an L7-4 linear array probe. The probe was positioned onto the flow phantom so that a longitudinal image of the flow channel could be obtained. All measurements were made in harmonic B-mode at a Mechanical Index of 1.0 and focused to a depth of 2.9 cm. For each test run, a total of 30 images were taken at a triggering rate of 30 pulses per minute and then digitally stored.

A vial of the lyophilized nanobubble product was reconstituted with 2 ml deionized water. A measured aliquot of the resulting nanobubble suspension was then added to the beaker which contained 500 ml deionized and degassed water. The pump was turned on to initiate flow of the nanobubble agent through the phantom. Once steady flow was attained, the acoustic imaging was begun.

The obtained images were analyzed by first establishing a representative "region of interest" on the image, taking a video densitometric reading of the region, and then calculating an average over the 30 acoustic images for each test run. The results of the study are displayed in the table below. The left column is the volume of reconstituted agent diluted into the 500 ml reservoir, the middle column is the average video density, and the right column is the coefficient of variability calculated as a percentage of one standard deviation over the average. Maximum video density is 1.0.

| microliters | video density | CV |
|---|---|---|
| 0 | $4.9 \times 10^{-7}$ | 83.3% |
| 18 | $1.19 \times 10^{-3}$ | 21.0% |
| 54 | $2.92 \times 10^{-3}$ | 17.3% |
| 125 | $5.06 \times 10^{-3}$ | 16.5% |

EXAMPLE 4

In-vitro Acoustic Study

A Hewlett Packard 5500 ultrasound scanner was used for this study in conjunction with an ATS Laboratories, Model 524 Doppler Flow Phantom. The S4 transducer was positioned vertically downward and oriented along the centerline of the 6 mm diameter flow tube within the phantom. Thus, the flow tube appeared as a constant diameter tube (dark interior) in the sector of the scan. The scanner was set in the harmonic mode (1.8/3.6 MHz) with a beam width of approximately 4 cm at the 4 cm depth of the tube centerline below the transducer. A peristaltic pump delivered liquid containing test agent from a 500 ml beaker placed on a magnetic mixer through the phantom and into a discharge container. This fluid was not recirculated. The fluid was stirred constantly in the beaker throughout the test. A nanobubble suspension produced in accordance with Example 2 (identified as M985) was placed in the beaker, thoroughly mixed with degassed water, and pumped through the phantom with a mean velocity of approximately one cm per second. Axial positions were marked on the scanner monitor and measured from the proximal end of the flow tube, as seen by the scanner, using the caliper function of the system. A circular region of interest (ROI) was selected for the study and used exclusively throughout. The triggering interval was set at 200 milliseconds for any acoustic densitometric (AD) measured made. Power levels were varied and 60 AD measurements were averaged for each power setting and each location.

Figure 4:
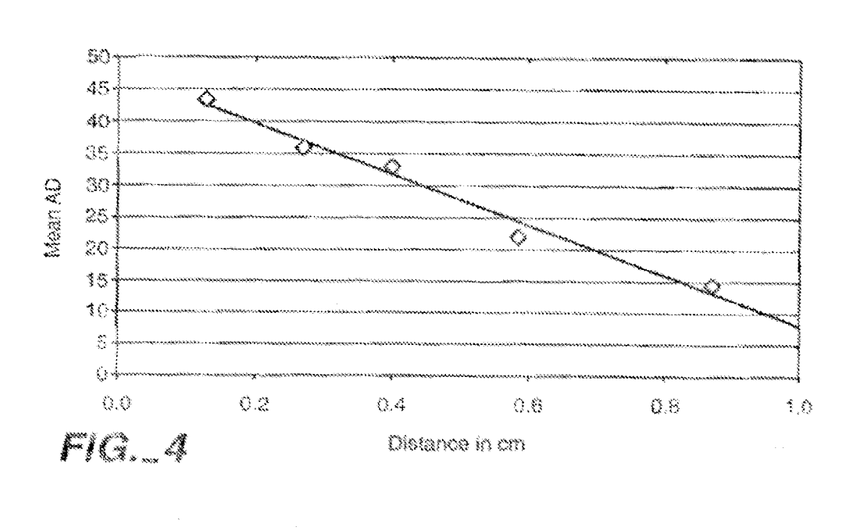
FIG. 4 is a plot of mean backscatter vs. distance from the scanner described in Example 4.
Figure 5:
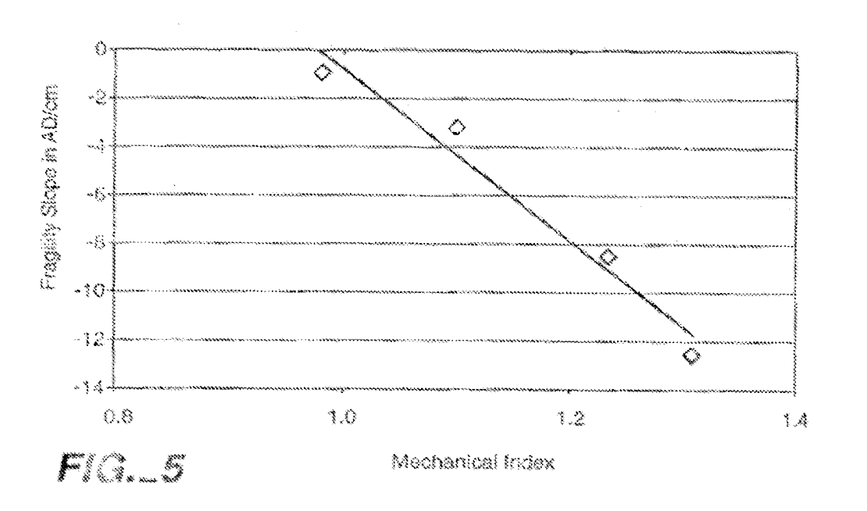
FIG. 5 is a plot of fragility slope vs. mechanical index described in Example 4.

With the described setup, an experiment was performed to determine the rupture characteristics of the nanobubble agent. If nanobubble destruction does not occur, the AD reading is constant along the flow phantom. If the nanobubbles do fail, there is a decrease in AD reading along the flow phantom, and there is a slope associated with this decease. This is shown in FIG. 4 below. A linear regression fit to the data permits the determination of the slope. This slope is plotted against MI as seen in FIG. 5 and this graph permits determination of the point where the agent begins to fail, i.e. when the slope becomes zero.

Examination of these results reveals that when the mechanical index exceeds about 1 (MI=1), the agent fails. Below this MI the agent remains intact.

EXAMPLE 5

In-vitro Acoustic Study

Figure 6:
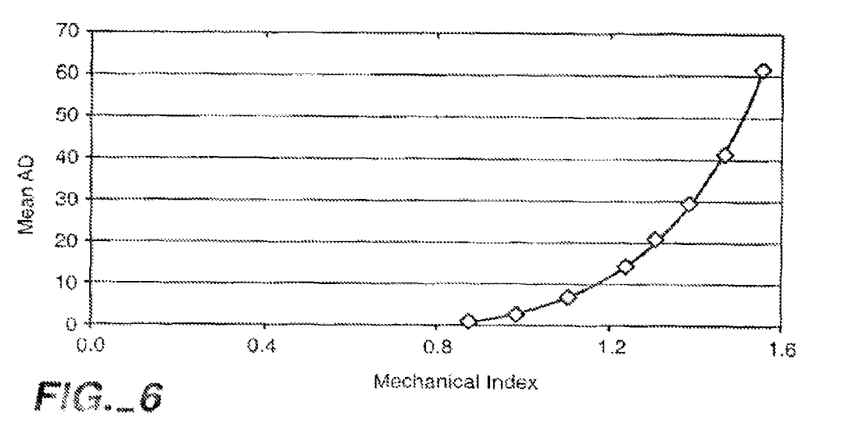
FIG. 6 is a plot of backscatter vs. mechanical index described in Example 5.

Using the experimental set-up as detailed in Example 4, backscatter AD measurements were made of a nanobubble agent produced in accordance with Example 2, herein identified as M985, as a function of Mechanical Index (MI). The results shown in FIG. 6 represent the peak backscatter response which was extrapolated back to zero cm. The value of MI was varied from a maximum of 1.6 to less than 0.9. Lower values were not attempted because the values of backscatter AD were too low to measure. It is noteworthy that the MI below which no significant backscatter AD is detected is similar to the critical MI determined in Example 4 suggesting that for this agent acoustic detection depends upon bubble destruction.

The enhanced acoustic signals are obtained during the process of bubble rupture by sound waves, that is the bubble echo cross-section increases above the unbroken bubble cross-section during destruction. To further demonstrate this for agent detection, the agent was exposed to four different MI levels for a period of time, two at or above the critical MI and two below. Agent M985 was sonicated continuously in the test system. In this case the nanobubble containing test fluid was recirculated thus providing multiple passes under the transducer. The nanobubble agent was divided into four equal amounts and exposed to four different power levels of continuous sonication for 30 minutes each. The MI levels selected were: 1.6, 1.0, 0.5, and as a control, 0 [the scanner was placed in the freeze mode for the latter]. Later, each sonicated sample was tested for backscatter in the same system and in the same manner described in Example 4. From these tests, peak AD was measured.

One would not expect a significant backscatter from intact bubbles from the test agent exposed to 30 minutes of sonication at levels exceeding the critical MI (MI=1.0, 1.6) since bubbles exposed to this intensity of insonation are expected to break and be lost to the test medium. However, for samples sonicated at levels of MI less than 1, one would expect good backscatter and a normal bubble count (MI=0.5, 0) since bubbles exposed to intensity of insonation are expected to remain intact.

Figure 7:
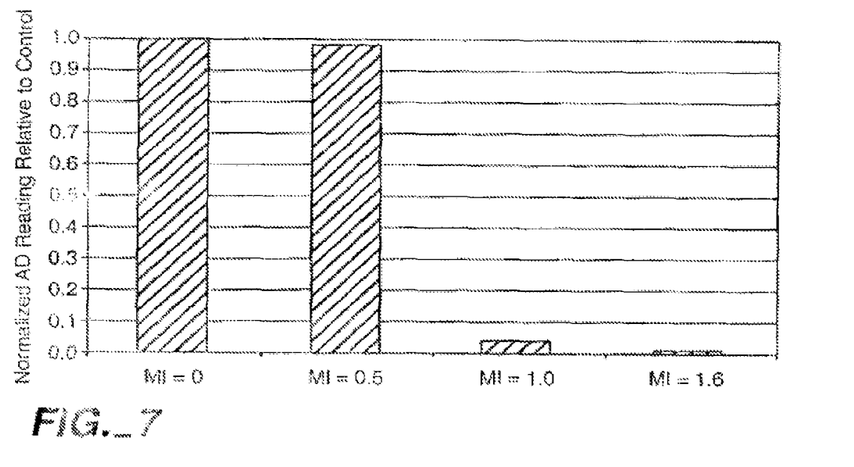
FIG. 7 is a plot of normalized backscatter of four different MI values described in Example 5.

The results, which conform to these expectations, are presented in FIG. 7 in normalized form relative to the zero MI (MI=0) test condition. Note that nearly all acoustic signals are lost for the samples sonicated with a MI of 1.0 or higher. Optical densitometric studies were performed following the 30 minutes of sonication and they too showed significant bubble destruction. The two samples sonicated at low power levels (MI<1.0) did not experience significant loss of backscatter AD. No significant change in bubble concentration were observed as judged by optical densitometry.

In Example 4 it was determined that the value of MI (called critical MI) where the agent M985 begins to break was almost 1.0. This was based upon the intercept of the fragility slope curve with the x-axis. We see from FIG. 6 that values of MI equal to or greater than this value did not produce measurable backscatter whereas the samples exposed to lesser values of MI were unaffected. FIG. 7 demonstrates that insonation at values of MI greater than the critical value cause loss of acoustic signals. Further, if we do not rupture the bubbles, we obtain full acoustic backscatter. It thus appears that in order to obtain significant backscatter from this agent, it is necessary to destroy it.

EXAMPLE 6

In-vivo Acoustic Study

The popliteal node of a canine model was easily detected using stimulated acoustic emission (SAE) imaging methods on an HP-5500 scanner. Nanobubbles prepared in accordance with Example 1 were used for the study. In the study test agent was injected subcutaneously into the metatarsal region of the dog. The arrival of agent into the popliteal node could be seen using SAE imaging within a few minutes post-injection. Accumulation of agent within the node could not be detected using B-mode imaging techniques.

What is claimed is:

1. A composition comprising a plurality of nanobubbles comprising a bilayered shell, wherein a majority of said plurality of nanobubbles have diameters in the range of about 100 to 800 nanometers, wherein said bilayered shell comprises an inner polymer layer and an outer cross-linked amphiphillic material layer enclosing a single gas-filled hollow core, wherein the said bilayered shell is rupturable upon exposure to ultrasound energy, and wherein the inner and outer layers are not covalently linked to one another.

2. The composition according to claim 1, wherein said gas is selected from the group consisting of air, a perfluorocarbon and nitrogen.

3. The composition according to claim 2, wherein said gas is nitrogen.

4. The composition according to claim 1, wherein said outer layer further comprises a surface-modifying agent.

5. The composition according to claim 4, wherein said surface-modifying agent is a targeting moiety for binding to a selected tissue.

6. The composition according to claim 4, wherein said surface-modifying agent is a polyethylene glycol.

7. The composition according to claim 1, wherein said cross-linked amphiphilic material is glutaraldehyde cross-linked human serum albumin, said biodegradable polymer is polylactide and said gas is nitrogen.

8. The composition according to claim 1 which further comprises a surfactant.

9. The composition according to claim 1, wherein said biodegradable polymer is selected from the group consisting of polycaprolactone, polylactide, polyglycolide, polyhydroxyvalerate, polyhydroxybutyrate, or copolymers thereof; delta-valerolactone, polyalkylcyanoacrylates, polyamides, polydioxanones, poly-beta-aminnoketones, polyanhydrides, poly-(ortho)esters, and polyamino acids.

10. The composition according to claim 9, wherein said biodegradable polymer is polylactide.

11. The composition according to claim 8, wherein said surfactant is selected from the group consisting of polyoxyalkylene fatty acid esters and poloxamers.

12. The composition according to claim 1 which further comprises a sugar.

13. The composition according to claim 12, wherein said sugar is selected from the group consisting of mannitol, sucrose, lactose and sorbitol.

14. The composition according to claim 1 which further comprises a synthetic water soluble polymer.

15. The composition according to claim 14, wherein said synthetic water-soluble polymer is selected from the group consisting of polyethylene glycol, polyvinyl pyrrolidone and dextran.

16. The composition according to claim 1 which further comprises an amino acid.

17. The composition according to claim 16, wherein said amino acid is selected from the group consisting of glycine, arginine and aspartic acid.

18. The composition according to claim 1, wherein the intensity and frequency of said ultrasound energy are suitable for ultrasound imaging.

19. The composition according to claim 1, wherein said cross-linked amphiphilic material is cross-linked protein.

20. The composition according to claim 19, wherein said protein is selected from the group consisting of collagen, gelatin, albumin, globulins, and derivatives and combinations thereof.

21. The composition according to claim 20, wherein said protein is albumin.

22. The composition according to claim 1, wherein said cross-linked amphiphilic material is cross-linked with a cross-linking agent selected from the group consisting of an aldehyde and a carbodiimide.

23. The composition according to claim 22, wherein said cross-linking agent is glutaraldehyde.

24. The composition according to claim 4, wherein the surface-modifying agent is a biomaterial that enhances uptake of said plurality of nanobubbles by the lymph system.

25. The composition according to claim 24, wherein said biomaterial is Immunoglobulin G.

26. A composition useful for ultrasound imaging, comprising a plurality of nanobubbles, a majority of which have diameter in the range of about 100 to 800 nanometers, each of which comprises a bilayered shell surrounding a hollow core that is filled with a gaseous contrast agent, wherein the inner layer of the bilayered shell comprises a biodegradable polymer, the outer layer of the bilayered shell comprises a cross-linked amphiphilic material, the inner and outer layers of the bilayered shell are not covalently linked to one another, and further wherein said plurality of nanobubbles do not include a drug or additional contrast agents.

* * * * *